United States Patent [19]

Drabek

[11] 3,948,940
[45] Apr. 6, 1976

[54] PESTICIDAL PHTHALIMIDO PHOSPHOROUS ESTER COMPOUNDS

[75] Inventor: Jozef Drabek, Allschwil, Switzerland

[73] Assignee: Ciba-Geigy Corporation, Ardsley, N.Y.

[22] Filed: Oct. 2, 1972

[21] Appl. No.: 293,875

[30] Foreign Application Priority Data
Oct. 4, 1971 Switzerland.................. 14464/71
July 27, 1972 Switzerland.................. 11230/72

[52] U.S. Cl. 260/326 E; 260/250 BC; 260/256.4 E; 260/293.85; 260/295 M; 260/326.5 A; 424/200
[51] Int. Cl.²................................... C07D 209/48
[58] Field of Search.............. 260/326 E, 326.5 A

[56] References Cited
UNITED STATES PATENTS

| | | | |
|---|---|---|---|
| 2,767,194 | 10/1956 | Fancher............................ | 260/326 |
| 3,355,353 | 11/1967 | Jamison........................... | 260/326 X |
| 3,450,713 | 6/1969 | Tolkmith et al................... | 260/326 |
| 3,821,246 | 6/1974 | Kishino et al.................... | 260/326 E |

Primary Examiner—Raymond V. Rush
Attorney, Agent, or Firm—Frederick H. Rabin; Philip P. Berestecki

[57] ABSTRACT

5'-[imidomethylene]-5-alkyl-O-alkyldithiophosphoric esters of the formula

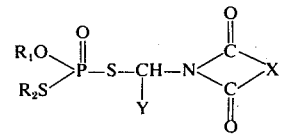

wherein
R₁ and R₂ are each alkyl,
X is alkylene, alkenylene, a carboxylic or nitrogen containing heterocyclic group, and
Y is hydrogen or CH₂—hal, hal being fluorine, chlorine, bromine or iodine, their manufacture and their use in pest control.

5 Claims, No Drawings

PESTICIDAL PHTHALIMIDO PHOSPHOROUS ESTER COMPOUNDS

This invention relates to S'-[imidomethylene]-S-alkyl-O-alkyldithiophosphoric esters, their manufacture and their use in pest control.

According to the present invention there are provided compounds of the formula

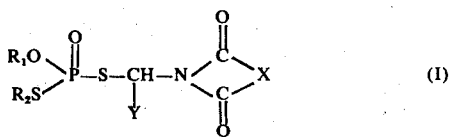

wherein $R_1$ and $R_2$ are each alkyl,

X is alkylene, alkenylene, a carbocyclic or nitrogen containing heterocyclic group, and Y is hydrogen or $CH_2$—hal, hal being fluorine, chlorine, bromine or iodine.

The alkyl groups for $R_1$ and $R_2$ and the alkylene and alkenylene groups for X can be branched or straight chain, and preferably have 1 to 5 or 2 to 5 carbon atoms in the chain respectively.

Examples of such groups include methyl, ethyl, n-propyl, isopropyl, n,-i-, sec- and tert-butyl, n-pentyl, —$CH_2CH_2$—, —$CH_2CH_2CH_2$—,

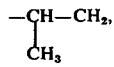

—CH=CH—,

In the scope of the present invention by carbocyclic rings are meant both substituted and unsubstituted rings such as:

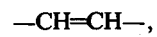

and for heterocyclic rings, unsubstituted rings, such as e.g. pyridine, pyrimidine, pyrazine rings.

Preferrred substituents on these rings are halogen, $C_1$–$C_4$ alkyl and/or nitro.

By halogen is meant fluorine, chlorine, bromine or iodine, preferably chlorine.

Preferred on account of their activity are compounds of formula I wherein $R_1$ and $R_2$ are each $C_1$–$C_5$ alkyl, X is —$CH_2CH_2$—, —$CH_2CH_2CH_2$—,

CH=CH—,

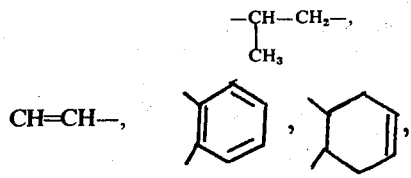

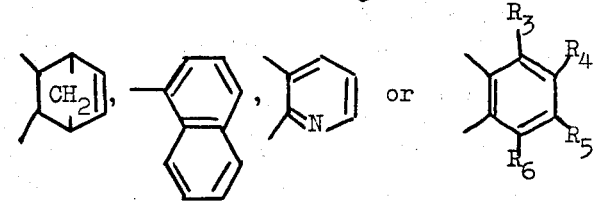

wherein $R_3$, $R_4$, $R_5$ and $R_6$ are each hydrogen, halogen, $C_1$–$C_4$ alkyl or nitro, Y is hydrogen or $CH_2$hal and hal is chlorine or bromine.

Particularly preferred, however on account of their activity, are compounds of the formula I in which $R_1$ is ethyl, $R_2$ is ethyl, n-propyl, isopropyl, n-butyl, isobutyl or n-pentyl, X is

and Y is hydrogen or $CH_2Br$.

The compounds of formula I can be made by the following known method:

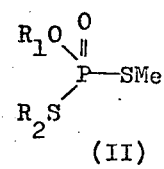

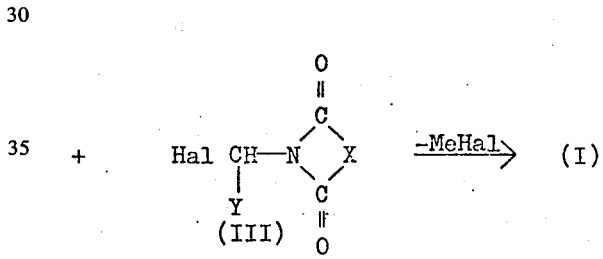

In formulae II and III, $R_1$, $R_2$, X and Y have the meanings given for formula I. Hal stands for fluorine, chlorine, bromine and iodine, preferably chlorine, and Me represents alkali metal, especially sodium or potassium, ammonium or alkylammonium.

The reaction is carried out at a temperature of 0° to 130° under normal pressure and preferably in an inert solvent medium.

For this, the following are suitable, for example: aromatic hydrocarbons such as benzene, toluene, petrol, chlorobenzene, polychlorobenzenes, bromobenzene, chlorinated alkanes with 1 to 3 carbon atoms; ethers such as dioxane, tetrahydrofuran; esters such as ethylacetate, ketones such as methyl, ethyl ketone, diethyl ketone, or nitriles such as acetonitrile.

The starting material of formulae II and III are partly known and can be made by methods known per se.

The compounds of formula I have a broad biocidal activity spectrum and can be used for combating the most varied animal and vegetable pests.

They are particularly suited to combating all development stages e.g. eggs, larvae, pupae, nymphs and adults of insects of the families: Tettigonidae, Gryllidae, Gryllotalpidae, Blattidae, Reduviidae, Phyrrhocoriae, Cimicidae, Aphididae, Diaspididae, Pseudococcidae, Scarabacidae, Dermestidae, Coccinellidae, Tenebrionidae, Chrysomelidae, Bruchidae, Tineidae, Noctuide, Lymatriidae, Pyralidae, Culcidae, Tipulidae, Stomoxydae, Trypetidae, Muscidae, Calliphoriade and Pulicidae, as well as Akarida of the families Ixodidae, Argasidae, Tetranychidae and Dermanyssidae.

The insecticidal or acaricidal action can be substantially broadened and matched to given circumstances by the addition of other insecticides and/or acarides.

As additives there are suitable, for example the following:

ORGANIC PHOSPHORUS COMPOUNDS

Bis- O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4-5-trichlorophenylthiophosphate (RONNEL)
O-ethyl-0,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-jodphenyl)-thiophosphate (JODOFENPHOS)
4-tert. butyl-2-chlorophenyl-N-methyl-O-methylamidophosphate (CRUFOMATE)
O,O-dimethyl-O-(3-methyl-4-methylmercapto-phenyl)thiophosphate (FENTHION)
Isopropylamino-O-ethyl-O-(4-methylmercapto-3-methylphenyl)-phosphate O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
O,O-dimethyl-O-($\alpha$-methylbenzyl-3-hydroxycrotonyl)phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxim-O,O-diethylthiophosphate (PHOXIM)
O,O-diethyl-O-(3-chloro-4-methyl-2-oxo-2-H-1-benzopyran-7-yl)-thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophosphate (PHOSALONE)
2-(diethoxyphosphinylimino)-1,3-dithiolane
O,O-dimethyl-S-[2-methoxy-1,3,4-thiadiazol-5-(4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)
O,O-diethyl-O-(2-isopropyl-4-methyl-6-pyrimidyl)-thiophosphate (DIAZINON)
O,O-diethyl-O-(2-chinoxalyl)thiophosphate
O,O-dimethyl-S-(4-oxo-1,2,3-benzotriazin-3(4H)-ylmethyl-dithiophosphate (AZINPHOSMETHYL)
O,O-diethyl-S-(4-oxo-1,2,3-benzotriazin-3(4H)-ylmethyl)-dithiophosphate (AZINPHOSETHYL)
S-[(4,6-diamino-s-triazin-2-yl)methyl]-O,O-dimethyldithiophosphate (MENAZON)
O,O-dimethyl-O-(3-chloro-4-nitrophenyl)thiophosphate (CHLORTHION)
O,O-dimethyl-O(or S)-2-(ethylthioethyl)thiophosphate (DEMETONS-METHYL)
2-(O,O-dimethyl-phosphoryl-thiomethyl)-5-methoxy-pyron-4-3,4-dichlorobenzyl-triphenyl-phosphoniumchloride
O,O-diethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)
O,O-diethyl-O-[2-diemthylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate 3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
0,2,4-dichlorophenyl-O-methylisopropylamidothiophosphate
O,O-diethyl-O-2,5-dichloro-4-bromophenylthiophosphate (BROMOPHOS-ETHYL)
Dimethyl-p-(methylthio)phenylphosphate
O,O-dimethyl-O-p-sulfamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane
Tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
Dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
Diethyl-S-2-(ethylsulphinyl)ethyl dithiophosphate (OXIDISULFOTON)
Bis-O,O-diethylthiophosphoric acid anhydride (SULFOTEP)
Dimethyl-1,3-di(carbomethoxy)-1-propen-2-yl-phosphate
Dimethyl-(2,2,2-trichloro-1-butyroyloxyethyl)phosphonate (BUTONATE)
O,O-dimethyl-O-(2,2-dichloro-1-methoxy-vinyl)-phosphate
Bis-(dimethylamido)fluorphosphate (DIMEFOX)
3,4-dichlorobenzyl-triphenylphosphoniumchloride
Dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
Diisopropylaminofluorophosphate (MIPAFOX)
O,O-dimethyl-S-(morpholinylcarbamoylmethyl)dithiophosphate (MORPHOTHION)
Bismethylamido-phenylphosphate
O,O-dimethyl-S-(benzene sulphonyl)dithiophosphate
O,O-dimethyl-(S and O)-ethylsulphinylethylthiophosphate
O,O-diethyl-O-4-nitrophenylphosphate
Triethoxy-isopropoxy-bis(thiophosphinyl)disulphide
2-methoxy-4H-1,3,2,benzodioxaphosphorin-2-oxide
Octamethylpyrophosphoramide (SCHRADAN)
Bis (dimethoxythiophospphinylsulphido)-phenylmethane
N,N,N',N'-tetramethyldiamidofluorophosphate (DIMEFOX)
O-phenyl-O-p-nitrophenyl-methanthiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethyl-phenyl)-thiophosphate
4,4'-bis-(O,O-dimethylthiophosphoryloxy)-diphenyl disulphide
O,O-di-(β-chloroethyl)-O-(3-chloro-4-methyl-coumarinyl-7)-phosphate
S-(1-phthalimidoethyl)-O,O-diethyldithiophosphate
O,O-dimethyl-O-(3-chloro-4-diethylsulphamyl-phenyl)-thiophosphate
O-methyl-O-(2-carbisopropoxyphenyl)-amidothiophosphate
5-(O,O-dimethylphosphoryl)-6-chloro-bicyclo(3.2.0)-heptadiene (1,5)
O-methyl-O-(2-i-propoxycarbonyl-1-methylvinyl)-ethylamidothiophosphate.

NITROPHENOLS AND DERIVATIVES 4,6-Dinitro, 6-methylphenol, Na-salt (dinitrocresol)
Dinitrobutylphenol (2,2',2'' triethanolamine salt)
2 cyclohexyl-4,6-dinitrophenol (dinex)
2-(1-methylheptyl)-4,6-dinitrophenyl-crotonate (dinocap)
2 sec.-butyl-4,6-dinitrophenyl-3-methyl-butenoate (binapacryl)
2 sec.-butyl-4,6-dinitrophenyl-cyclopropionate
2 sec.-butyl-4,6-dinitrophenyl-isopropyl-carbonate (dinobuton)

MISCELLANEOUS pyrethin I
pyrethin II 3-allyl-2-methyl-4-oxo-2-cyclopentan-1-yl-chrysanthemumate (Allethrin)
6-chloriperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxol, 3-dithiolo-[4,5-b]-quinoxaline [Quinomethionate]
(I)-3-(2-furfuryl)-2-methyl-4-oxocyclopent-2-enyl-(I)-(cis+trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbanyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide (chlorobenside)
2-thio-1,3-dithiolo-(,5-6)-quinoxaline (thioquinox)
prop-2-ynyl-(4-t-butylphenoxy)-cyclohexylsulphite (propargil)

FORMAMIDINES 1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl)-formamidine
1-n-butyl-2-(2'-methyl-4'-chlorophenyl-imino)-pyrrolidine.

UREA

N-2-methyl-4-chlorophenyl-N',N'-dimethyl-thiourea.

CARBAMATES 1-naphthyl-N-methyl carbamate (CARBARYL)
2-butinyl-4-chlorophenyl carbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methyl carbamate (CPMC)
5-chloro-6-oxo-2-norbonan-carbonitril-O-(methylcarbamoyl)oxime
1-(dimethylcarbamoyl)-5-methyl-3-pyrazolyl-N,N-dimethyl carbamate (DIMETILAN)
2,3-dihydro-2,2-dimethyl-7-benzofuranyl-N-methyl carbamate (CARBOFURAN)
2-methyl-2-methylthio-propionaldehyde-O-(methyl carbamoyl)-oxime (ALDICARB)
8-Quinaldyl-N-methylcarbamate and its salts
Methyl 2-isopropyl-4-(methylcarbamoyloxy)carbanilate
m-(1- ethylpropyl)phenyl-N-methylcarbamate
3,5-Di-tert. butyl-N-methylcarbamate
m-(1-Methylbutyl)phenyl-N-methylcarbamate
2-Isopropylphenyl-N-methylcarbamate
2-sec. Butylphenyl-N-methylcarbamate
m-Tolyl-N-methylcarbamate
2,3-Xylyl-N-methylcarbamate
3-Isopropylphenyl-N-methylcarbamate
3-tert.Butylphenyl-N-methylcarbamate
3-sec.-Butylphenyl-N-methylcarbamate
3-Isopropyl-5-methylphenyl-N-methylcarbamate (PROMECARB)
3,5-Diisopropylphenyl-N-methylcarbamate
2-Chlor-5-isopropylphenyl-N-methylcarbamate
2-Chlor-4,5-dimethylphenyl-N-methylcarbamate
2-(1,3-Dioxolan-2-yl)phenyl-N-methylcarbamate (DIOXACARB)
2-(4,5-Dimethyl-1,3-dioxolan-2-yl)phenyl-N-methylcarbamate
2-(1,3-Dioxan-2-yl)phenyl-N-methylcarbamate
2-(1,3-Dithiolan-2-yl)phenyl-N-methylcarbamate
2-(1,3-Dithiolan-2-yl)phenyl-N,N-dimethylcarbamate
2- Isopropyoxyphenyl-N-methylcarbamate (ARPROCARB)
2-(2-Propinyloxy)phenyl-N-methylcarbamate
3-(2-Propinyloxy)phenyl-N-methylcarbamate
2-Dimethylaminophenyl-N-methylcarbamate
2-Diallylaminophenyl-N-methylcarbamate
4-Diallylamino-3,5-xylyl-N-methylcarbamate (ALLYXICARB)
4-Benzothienyl-N-methylcarbamate
2,3-Dihydro-2-methyl-7-benzofuranyl-N-methylcarbamate
3-Methyl-1-phenylpyrazol-5-yl-N,N-dimethylcarbamate
1-Isopropyl-3-methylpyrazol-5-yl-N,N-dimethylcarbamate (ISOLAN)
2-Dimethylamino-5,6-dimethylpyrimidin-4-yl-N,N-dimethylcarbamate
3-Methyl-4-dimethylaminomethyleniminophenyl-N-methylcarbamate
3,4-dimethylphenyl-N-methylcarbamate
2-cyclopentyl-N-methylcarbamate
3-Dimethylamino-methyleniminophenyl-N-methylcarbamate (FORMETANATE) and its salts
1-Methylthio-ethylimino-N-methylcarbamate (METHOMYL)
2-Methylcarbamoyloximino-1,3-dithiolane
5-Methyl-2-methylcarbamoyloximino-1,3-oxythiolane
2-(1-Methoxy-2-propoxy)phenyl-N-methylcarbamate
2-(1-Butin-3-yl-oxy)phenyl-N-methylcarbamate
1-Dimethylcarbamyl-1-methylthio-O-methylcarbamyl-formoxime
1-(2'-Cyanoethylthio)-O-methylcarbamyl-acetaldoxime
1-Methylthio-O-carbamyl-acetaldoxime
O-(3-sec.-Butylphenyl)-N-phenylthio-N-methylcarbamate
2,5-Dimethyl-1,3-dithiolan-2-(O-methylcarbamyl)-aldoxime O-2-Diphenyl-N-methylcarbamate
2-(N-Methylcarbamyl-oximino)-3-chlor-bicyclo[2.2.1]heptane
2-(N-Methylcarbamtl-oximino)-bicyclo[2.2.1]heptane
3-Isopropylphenyl-N-methyl-N-chloracetyl-carbamate
3-Isopropylphenyl-N-methyl-N-methylthiomethylcarbamate
O-(2,2-Dimethyl-4-chlor-2,3-dihydro-7-benzofuranyl)-N-methylcarbamate
O-(2,2,4-Trimethyl-2,3-dihydro-7-benzofuranyl)-N-methylcarbamate
O-Naphthyl-N-methyl-N-acetyl-carbamate
O-5,6,7,8-Tetrahydronaphthyl-N-methylcarbamate
3-Isopropyl-4-methylthio-phenyl-N-methylcarbamate
3,5-Dimethyl-4-methoxy-phenyl-N-methylcarbamate
3-Methoxymethoxy-phenyl-N-methylcarbamate
3-Allyloxyphenyl-N-methylcarbamate
2-Propargyloxymethoxy-phenyl-N-methylcarbamate
2-Allyloxyphenyl-N-methycarbamate
4-Methoxycarbonylamino-3-isopropylphenyl-N-methylcarbamate
3,5-Dimethyl-4-methoxycarbonylamino-phenyl-N-methylcarbamate
2-γ-Methylthiopropylphenyl-N-methylcarbamate
3-(α-Methoxymethyl-2-propenyl)-phenyl-N-methylcarbamate
2-Chlor-5-tert-butyl-phenyl-N-methylcarbamate
4-(Methyl-propargylamino)-3,5-xylyl-N-methylcarbamate
4-(Methyl-γ-chlorallylamino)-3,5-xylyl-N-methylcarbamate
4-(Methyl-β-chlorallylamino)-3,5-xylyl-N-methylcarbamate
1-(β-Aethoxycarbonylethyl)-3-methyl-5-pyrazolyl-N,N-dimethylcarbamate
3-Methyl-4-(dimethylamino-methylmercapto-methylenimino)phenyl-N-methylcarbamate
1,3-Bis(carbamoylthio)-2-(N,N-dimethylamino)-propanhydrochloride
5,5-Dimethylhydroresorcinoldimethylcarbamate
2-[Ethylpropargylamino]-phenyl-N-methylcarbamate
2-[Ethylpropargylamino]-phenyl-N-methylcarbamate
2-[Dipropargylamino]-phenyl-N-methylcarbomate
4-[Dipropargylamino]-3-tolyl-N-methylcarbomate
4-[Dipropargylamino]-3,5-xylyl-N-methylcarbamate
2-[Allyl-isopropylamino]-phenyl-N-Methylcarbamate
3-[Allyl-isopropylamino]- phenyl-N-methylcarbamate

CHLORINATED HYDROCARBONS

γ-hexachlorocyclohexane [GAMMEXANE; LINDAN; γ HCH]
1,2,3,4,5,6,7,8,8-octachloro-3α,4,7,7α'tetrahydro-4,7-methylenindane [CHLORDAN]
1,4,5,6,7,8,8-heptachloro,3α,4,7,7α-tetrahydro-4,7-methylenindane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8-,8α-octahydro-exo-1,4-endo-5,6-dimethanonapthalene [DIELDRIN]
1,2,3,4,10,10-hexachloro-6,7-epoxy-1,4,4α,5,6,7,8-,8α-octahydro-endo-endo-5,8-dimethanonaphtalene [ENDRIN].

Moreover, the compounds of the formula I possess nematocidal properties and may be used, for example, to combat the following plant parasitic nematodes: Meloidogyne spp., Heterodera spp., Ditylenchus spp., Pratylenchus spp., Para- The compounds of formula I can be used alone or together with suitable carriers and/or additives. Suitable carriers or additives can be solid or liquid and correspond to materials customarily used in formulation technique such as e.g. natural or regenerated materials, solvents, dispersing agents, wetting agents, adhesives, thickeners, binders and/or fertilisers.

For application the compounds of formula I can be processed by means of generally known techniques to dusts, emulsion concentrates, granules, dispersions, sprays, solutions or suspensions in the usual way. Cattle dips and spray races, in which aqueous preparations are used should also be mentioned.

The agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:

Solid forms:
dusts, tracking agents, granules, coated granules, impregnated granules and homogeneous granules.

Liquid forms:
a. active substance concentrates which are dispersible in water: wettable powders, pastes, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc, each used alone or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenyl and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleyl methyl tauride, ditertiary ethylene glycols, dialkyl dilauryl ammonium chloride and fatty acid alkali and alkaline earth metal salts.

Suitable anti-foam agents are silicone oils.

The active substances are so mixed, ground, sieved and strained with the addtivies mentioned above that, in wettable powders, the solid particle size of from 0.02 to 0.04 and in pastes, of 0.03 mm is not exceeded. To produce emulsifiable concentrates and pastes, dispersing agents such as those given in the previous paragraphs, organic solvents and water are used. Examples of suitable solvents are the following: alcohols, benzene, xylene, toluene, dimethyl sulfoxide, and mineral oil fractions boiling between 120° and 350°C. The solvents must be practically odorless, not phytotoxic, and inert to the active substances.

Furthermore, the agents according to the invention can be applied in the form of solutions. For this purpose the active substance or several active substances of general formula I are dissolved in suitable organic solvents, mixtures of solvents or in water. Aliphatic and aromatic hydrocarbons, chlorinated derivatives thereof, alkyl naphthalenes, and mineral oils alone or mixed with each other, can be used as organic solvents.

The content of active substance in the above described agents is between 0.1 to 95%, in which connection it should be mentioned that in the case of application from aircraft or some other suitable means of application, it is possible to use concentrations of up to 99.5% or even pure active substance.

The active substances of the formula I can, for example, be formulated as follows:

DUSTS

The following substances are used to manufacture (a) a 5% and (b) a 2% dust:

a.
  5 parts of active substance
  95 parts of talcum b.
  2 parts of active substance
  1 part of highly disperse silicic acid
  97 parts of talcum.

The active substances are mixed with the carriers and ground.

GRANULES

The following substances ae used to manufacture 5% granules:
  5 parts of active substance
  0.25 part of epichlorohydrin
  0.25 part of cetyl polyglycol ether
  3.50 parts of polyethylene glycol
  91 parts of kaolin (particle size = 0.3–0.8 mm).

The active substance is mixed with epichlorohydrin and the mixture dissolved with 6 parts of acetone, then polyethylene glycol and cetyl polyglycol ether are added. The resulting solution is sprayed on kaolin and the acetone is subsequently evaporated in vacuo.

WETTABLE POWDER

The following constituents are used to manufacture an (a) 40%, (b) and (c) 25% and (d) 10% wettable powder:

a.
  40 parts of active substance
  5 parts of sodium lignin sulphonate
  1 part of sodium dibutylnaphthalenesulphonic acid
  54 parts of silicic acid b.
  25 parts of active substance
  4.5 parts of calcium lignin sulphonate
  1.9 parts of Champagne chalk/hydroxyethyl cellulose mixture (1:1)
  1.5 parts of sodium dibutylnaphthalenesulphonate
  19.5 parts of silicic acid
  19.5 parts of Champagne chalk
  28.1 parts of kaolin;

c.
  25 parts of active substance
  2.5 parts of isooctylphenoxy-polyoxyethylene ethanol 1.7 parts of Champagne chalk/hydroxyethyl cellulose mixture (1:1)
8.3 parts of sodium aluminium silicate
16.5 parts of kieselguhr
46 parts of kaolin;

d.
10 parts of active substance
3 parts of mixture of sodium salt of saturated fatty alcohol sulphates
5 parts of naphthalenesulphonic acid/formaldehyde condensate
82 parts of kaolin.

The active substances are intimately mixed in appropriate mixing device with the adjuvants and ground in corresponding mills and rollers. Wettable powder are obtained which can be diluted with water to suspensions of every desired concentration.

EMULSIFIABLE CONCENTRATES

The following substances are used to manufacture (a) a 10% and (b) a 25% emulsifiable concentrate:

a.
10 parts of active substance
3.4 parts of epoxidised vegetable oil
13.4 parts of a combination emulsifier consisting of fatty alcohol polyglycol ether and calcium alkylarylsulphonate
40 parts of dimethyl formamide
43.2 parts of xylene;

b.
25 parts of active substance
2.5 parts of epoxidised vegetable oil
10 parts of an alkylarylsulphonate/fatty alcohol polyglycol ether mixture
5 parts of dimethyl formamide
57.5 parts of xylene.

Emulsion of every desired concentration can be manufactured by diluting these concentrates with water.

SPRAYS

The following constituents are used to manufacture a 5% spray:
5 parts of active substance
1 part of epichlorohydrin
94 parts of petrol (boiling range 160°–190°C)

The following examples will serve to illustrate the manufacture and activity of the compounds.

EXAMPLE 1

Manufacture of O-ethyl-S-n-propyl-S-phthalimido methylene dithiophosphoric acid ester 40.5g of the potassium salt of O-ethyl-,S'-n-propyldithiophosphoric acid and 29.3g N-chloromethylene phthalic acid imide were stirred for 5 hours at 60°C in 250 ml acetonitrile. At the end of the reaction the mixture was poured into water and the separated oil taken up in 200 ml benzene. After washing with water, the benzenic solution was dried over sodium sulphate. After distilling off 42.7g (79% of theory) of the compound of the formula

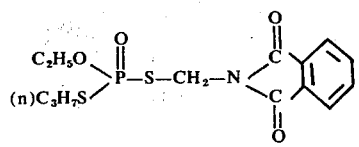

was obtained, as a yellow oil with a refractive index $n_D^{25}$:1.5764.

In a similar fashion the following compounds were manufactured

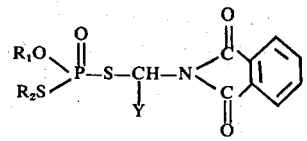

| $R_1$ | $R_2$ | Y | Physical Data |
|---|---|---|---|
| $C_2H_5$ | $(n)C_4H_9$ | H | $n_D^{20} = 1,5734$ |
| $C_2H_5$ | $C_2H_5$ | H | $n_D^{20} = 1,5890$ |
| $C_2H_5$ | $(i)C_3H_7$ | H | $n_D^{20} = 1,5794$ |
| $C_2H_5$ | $(i)C_4H_9$ | H | $n_D^{20} = 1,5754$ |
| $C_2H_5$ | $(n)C_5H_{11}$ | H | $n_D^{20} = 1,5715$ |
| $C_2H_5$ | $(n)C_4H_9$ | $-CH_2Br$ | $n_D^{20} = 1,5837$ |
| $C_2H_5$ | $(n)C_3H_7$ | $-CH_2Br$ | $n_D^{20} = 1,5902$ |
| $C_2H_5$ | $(i)C_4H_9$ | $-CH_2Br$ | $n_D^{20} = 1,5842$ |
| $C_2H_5$ | $(n)C_5H_{11}$ | $-CH_2Br$ | $n_D^{20} = 1,5803$ |

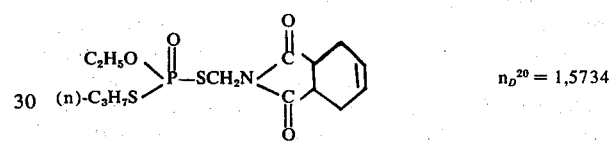

$n_D^{20} = 1,5734$

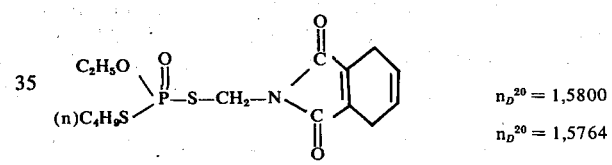

$n_D^{20} = 1,5800$ $n_D^{20} = 1,5764$

EXAMPLE 2

A. Insecticidal ingest poison action

Tobacco and potato plants are sprayed with a 0.05% aqueous emulsion (obtained from a 10% emulsifiable concentrate).

After the coating has dried, Egyptian cotton leaf worms (*Spodoptera litoralis*) are settled on the tobacco plants and Colarado potato beetle larvae (*Leptinotarsa decemlineata*) on the potato plants. The test is carried out at 24°C and 60% relative humidity.

The compounds according to Example I have an ingest poison action against *Spodoptera litoralis* and *Leptinotarsa decemlineata*.

B. Systemic insecticidal action

To determine the systemic action, rooted bean plants (*Vicia fabae*) are put into a 0.01% aqueous active substance solution (obtained from a 10% emulsifiable concentrate). After 24 hours, aphids (*Aphis fabae*) are placed on the parts of the plant above the soil. The aphids are protected from contact and gas action by means of a special device. The test is carried out at 24°C and 70% relative humidity.

In the above tests the compounds according to Example I displayed insecticidal ingest poison action and systemic insecticidal action.

EXAMPLE 3

Action against Chilo supressalis

Six rice plants at a time of the variety Caloro were transplanted into plastic pots (diameter at the top = 17 cm) and reared to a height of about 60 cm. Infestation with Chilo supressalis larvae ($L_1$; 3–4 mm long) took place 2 days after application of the active substance in granule form to the paddy water (rate of application: 8 kg of active substance per hectare). Evaluation of the insecticidal action took place 10 days after application of the granules.

The compounds according to Example I were active in the above test against Chilo suppressalis.

EXAMPLE 4

Sterilised compost earth was homogeneously mixed with a wettable powder containing 25% of active substance so that there resulted a rate of application of 8 kg of active substance per hectare.

Young zucchetti plants (*Cucumis pepo*) were put into plastic pots with the treated soil (3 plants per pot; diameter of pot = 7 cm). Each pot was infected immediately afterwards with 5 *Aulacophora femoralis* and *Pachmoda* or *Chortophila* larvae. The control was carried out 4, 8, 16 and 32 days after depositing the larvae.

At 80–100% kill after the first control, a fresh infestation with 5 larvae each was carried out in the same soil sample with 3 new succhetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example I displayed action against *Aulacophora femoralis*, *Pachmoda* and *Chortophila* larvae.

EXAMPLE 5

Action against ticks

A. *Rhicephalus bursa*

In each of the two test series 5 adult ticks and 50 tick larvae are counted into a glass tube and immersed for 1 to 2 minutes in 2 ml of an aqueous emulsion from an emulsion series each containing 100, 10, 1 and 0.1 ppm of test substance. The tube is then sealed with a standardised cotton wool plug and placed on its head, so that the active substance emulsion can be absorbed by the cotton wool.

In the case of the adults evaluation takes place after 2 weeks, and in that of the larvae after 2 days. Each test is repeated twice.

B. *Boophilus microplus* (larvae)

Tests are carried out in each case with 20 OP-sensitive or OP resistance larvae using an analogous dilution series as in the case of test A. (Resistance relates to tolerance of diazinone).

The compounds according to Example 1 act in these tests against adults and larvae of *Rhipicephalus bursa* and sensitive and OP resistant larvae of *Boophilus microplus*.

EXAMPLE 6

Acaricidal action

*Phaseolus vlugaris* (dwarf beans) have an infested piece of leaf from a mass culture of *Tetranychus urticae* placed on them 12 hours before the test for the acaricidal action. The occupying mobile stages are sprayed with the emulsified test preparations from a chromatography atomiser so that the spray broth does not run off. The number of living and dead larvae, adults and eggs are evaluated after 7 days under a stereoscopic microscope and the result expressed in percentages. During the "interim", the treated plants are kept in greenhouse compartments at 25°C.

The compounds according to Example I are active in the above test against eggs, larvae and adults of *Tetranychus urticae*.

EXAMPLE 7

Action against soil nematodes

To test the action against soil nematodes, the active substance (in the concentration indicated in each case is applied to and intimately mixed with soil infected with root gall nematodes (*Meloidgyne arenaria*). Immediately afterwards, tomato cuttings are planted in the thus prepared soil in a series of tests and after a waiting time of 8 days tomato seeds are sown in another test series.

In order to assess the nematocidal action, the galls present on the roots are counted 28 days after planting and sowing respectively. The compounds according to Example I display good action against *Meloidgyne arenaria* in this test.

What I claim is:

1. A compound of the formula $$\begin{array}{c} C_2H_5O \\ R_2S \end{array} \!\!\! P \!\!\! \begin{array}{c} O \\ S-CH-N \\ CH_2Br \end{array} \!\!\! \begin{array}{c} O \\ \| \\ C \\ | \\ C \\ \| \\ O \end{array} \!\!\! \bigcirc$$

in which $R_2$ is ethyl, n-propyl, isopropyl, n-butyl, isobutyl or n-pentyl.

2. The compound according to claim 1.

$$\begin{array}{c} C_2H_5O \\ (n)C_4H_9S \end{array} \!\!\! P \!\!\! \begin{array}{c} O \\ \| \\ S-CH-N \\ CH_2Br \end{array} \!\!\! \begin{array}{c} O \\ \| \\ C \\ | \\ C \\ \| \\ O \end{array} \!\!\! \bigcirc$$

3. The compound according to claim 1.

$$\begin{array}{c} C_2H_5O \\ (n)C_3H_7S \end{array} \!\!\! P \!\!\! \begin{array}{c} O \\ \| \\ S-CH-N \\ CH_2Br \end{array} \!\!\! \begin{array}{c} O \\ \| \\ C \\ | \\ C \\ \| \\ O \end{array} \!\!\! \bigcirc$$

4. The compound according to claim 1.

$$\begin{array}{c} C_2H_5O \\ (i)C_4H_9S \end{array} \!\!\! P \!\!\! \begin{array}{c} O \\ \| \\ S-CH-N \\ CH_2Br \end{array} \!\!\! \begin{array}{c} O \\ \| \\ C \\ | \\ C \\ \| \\ O \end{array} \!\!\! \bigcirc$$

5. The compound according to claim 1.

$$\begin{array}{c} C_2H_5O \\ (n)C_5H_{11}S \end{array} \!\!\! P \!\!\! \begin{array}{c} O \\ \| \\ S-CH-N \\ CH_2Br \end{array} \!\!\! \begin{array}{c} O \\ \| \\ C \\ | \\ C \\ \| \\ O \end{array} \!\!\! \bigcirc$$

* * * * *